United States Patent [19]

Lepienne et al.

[11] Patent Number: 4,721,674

[45] Date of Patent: Jan. 26, 1988

[54] PROCESS FOR OBTAINING LYSOZYME BY A MICRO FILTRATION FROM A STARTING MATERIAL BASED ON WHITE OF EGG

[75] Inventors: Alain Lepienne, Chartres; Jean-Louis Maubois, Pacé ; Michel Thireau, Bethune; Michel Piot, Rennes-Saint Grégoire, all of France

[73] Assignee: Institut National de la Recherche Agronomique, Paris, France

[21] Appl. No.: 769,380

[22] Filed: Aug. 26, 1985

[30] Foreign Application Priority Data

Aug. 28, 1984 [FR] France ............... 84 13305

[51] Int. Cl.$^4$ .............. C12N 9/36; A61K 37/54; A23J 1/08
[52] U.S. Cl. .............................. 435/206; 435/814; 530/368
[58] Field of Search ............... 435/206; 530/368

[56] References Cited

U.S. PATENT DOCUMENTS 4,504,583  3/1985  Hasegawa et al. ............... 435/206
4,552,845  11/1985  Reid ............................. 435/206

FOREIGN PATENT DOCUMENTS 1399090  6/1975  United Kingdom ............... 530/368

OTHER PUBLICATIONS

Le et al., Chemical Abstracts, vol. 102:58255e, (1985).
Le et al., Chemical Abstracts, vol. 102:94255m, (1985).
Chemical Abstracts, vol. 96, No. 9, p. 251, No. 64850s, (Mar. 1, 1982).
Chemical Abstracts, vol. 94, No. 17, p. 388, No. 135510c, (Apr. 27, 1981).
Chemical Abstracts, vol. 97, No. 19, p. 348, No. 158929x, (Nov. 8, 1982).

*Primary Examiner*—Lionel M. Shapiro
*Attorney, Agent, or Firm*—Sandler & Greenblum

[57] ABSTRACT

A fluid starting material based on white of egg is subjected to at least one microfiltration by bringing the said material into contact, under pressure and in tangential flow, with a membrane capable of separating off the particles having a size of between about 0.02 micron and 10 microns, giving, firstly, a microfiltrate which passes through the membrane and contains at least a fraction of the lysozyme of the starting material and, secondly, a product held back by the membrane, which retains the natural properties of the starting material based on white of egg but is depleted in lysozyme. The obtained lysozyme can be conventionally used in particular in cheese-making.

11 Claims, No Drawings

PROCESS FOR OBTAINING LYSOZYME BY A MICRO FILTRATION FROM A STARTING MATERIAL BASED ON WHITE OF EGG

BACKGROUND OF THE INVENTION

The present invention relates to a novel process for the preparation of lysozyme or muramidase (E.C.3.2.1.17) from a starting material based on white of egg, using the microfiltration technique.

Lysozyme is present in the majority of physiological fluids (saliva, tears, female's milk). The principal industrial source of lysozyme is chicken white of egg, which contains 3 to 6 g of lysozyme/kg. The enzymatic properties of this protein result in it having a bactericidial action, essentially against Gram-positive bacteria. Its antibacterial properties are utilised for preventive purposes such as a supplement to mother's milk, and for curative purposes in the form of medicines against coughing, certain conditions of the mouth, and others. Over the last decade, the field of use of lysozyme has extended considerably because of its utilisation in the cheese-making industry. Lysozyme is in fact used to prevent the development of the butyric acid flora of milks intended for the manufacture of Emmental.

For the purposes of the present invention, the term "starting material based on white of egg" embraces white of egg itself and/or whole of egg as well as mixtures of these products with various additives, as will be described in more detail below.

Whole of egg is a mixture of white of egg and egg yolk in varying proportions (40 to 80% of white). The typical composition of industrial egg yok is as follows:

| water | proteins | lipids | carbohydrates | minerals |
| --- | --- | --- | --- | --- |
| 44–50% | 15.7–16.6 | 31.8–35.5 | 0.2–1 | 1.1 |

Industrial white of egg is obtained by breaking eggs so as to make it possible to release the contents of the egg and to separate the white of egg from the egg yolk. The average composition by weight of industrial white of egg is as follows:

| water | proteins | lipids | carbohydrates | minerals |
| --- | --- | --- | --- | --- |
| 88.5% | 10.5 | traces | 0.5 | 0.5 |

Proteins represent the major component of the solids: the ratio of nitrogen-containing materials to solids is generally greater than 90%. The pH of fresh white of egg, immediately after breaking the egg, is between 9 and 9.5. Industrial white of egg is essentially used in the biscuit-making industry because of its swelling proerties.

A dozen proteins can have identified in white of egg. Their respective contents and properties have also been described. Lysozyme is one of the proteins of white of egg and differs from the other proteins in respect of two essential characteristics:

its very low molecular weight (14,600 Daltons), which means that it is the smallest of the proteins in white of egg, and its high electropositive charge at the pH of white of egg (its isoelectric pH is in fact 10.7).

The current processes for the extraction of lysozyme from white of egg are based precisely on one or the other of these properties. These are three principal techniques, of which two are used industrially.

The chromatographic ion exchange techniques make use of the electrical characteristics of lysozyme. The principle of this type of process consists of fixing the lysozyme on cation exchange resins and then desorbing the lysozyme by means of an eluting solution. The nature of the resin can vary.

Such a process makes it possible to achieve a yield of lysozyme extraction of about 70%, but is complicated to put into operation and requires high technical skill from the personnel. Moreover it results in the production of an amount of polluting effluent at least equal to the amount of white of egg treated.

The second industrial technique consists of precipitating the lysozyme by starting out the white of egg at near its isoelectric pH (pH 9.5). The extraction yield is of the order of 60%; the process is simple but it has the major disadvantages that the white of egg is handled for 72 hours and that the by-product, namely salted white of egg, has poorer functional properties (in particular, poorer swellability) and is of limited usefulness (especially in the meat industries).

Finally, the last technique consists of molecular sieving of the proteins of white of egg on ultrafiltration membranes. These membranes are used conventionally in agro-foodstuffs industries to concentrate and purify liquid products before drying, by removing a part of the water and of the dissolved substances which they contain. Documents illustrating the ultrafiltration technique in the field of white of egg treatment are French Pat. No. A-2 157 826 and the articles cited in Chemical Abstracts, vol. 96, no. 9, 1st Mar. 1982, page 251, no. 64850s, Columbus, Ohio, US; L. V. KRYLOVA and al,: "Study of the effect of external factors on the ultrafiltration of water-salt solutions of lysozyme" & Deposited Doc. 1980, VINITI 3601-80, 14 pp. and Chemical Abstracts, vol. 94, no. 17, Apr. 27, 1981, page 388, no. 135510c, Columbus, Ohio, US: K. C. INGHAM and al: "Separation of macromolecules by ultrafiltration: influence of protein adsorption, protein-protein interactions, and concentration polarization" & Polym. Sci. Technol. 1980, 13 (Ultrafiltr. Membr. Appl.) 141–58. The low yield of the method (about 25% of the lysozyme present in the white of egg) prevents its development in industry.

The present invention relates to a process which overcomes the disadvantages of the prior art. It relates in particular to a process for the extraction of lysozyme from white of egg and/or whole of egg; the process can advantageously be carried out on an industrial scale and in particular gives a high extraction yield while making it possible to obtain, at one and the same time, a very pure lysozyme and a whole of egg and/or white of egg which is depleted in lysozyme but retains all the properties of the natural product.

The invention accordingly relates to a process for obtaining lysozyme from a starting material based on white of egg, wherein a fluid starting material based on white of egg, the starting material being as defined in the present description, is subjected to at least one microfiltration by bringing the said material into contact, under pressure and in tangential flow, with a membrane capable of separating off the particles having a size of between about 0.02 micron and 10 microns. This yields firstly, a microfiltrate which passes through the membrane and contains at least a fraction of the lysozyme of the starting material and, secondly, a product which is held back by the membrane and retains the functional properties of the starting material based on white of egg but is depleted in lysozyme.

Thus, the present invention consists in applying the industrial technique of microfiltration to the extraction of lysozyme from white of egg and/or whole of egg. Microfiltration is a known technique for separating or removing particles, cf., for example, the work by H. W. Ballew entitled "Basics of filtration and separation" (1978). According to this technique, the starting material is brought into contact with a membrane having certain porosity characteristics. This contact is effected under pressure, in tangential flow, so as to force a fraction—the so-called microfiltrate—of the product to pass through the membrane. As stated in the abovementioned work by H. W. Ballew, the fundamental difference between ultrafiltration and microfiltration is that ultrafiltration makes it possible to separate molecules whilst microfiltration has the object of separating particles. The two techniques thus essentially differ in respect of the nature of the membranes employed. In the case of microfiltration, the membranes have a pore diameter at least a hundred times greater than that of the ultrafiltration membranes. Contrary to the latter, which theoretically only allow water and non-protein dissolved substances to pass, the microfiltration membranes only retain microorganisms, and colloidal or micellar substances.

The ultrafiltration membranes are applied to the selective concentrating of protein materials in agro-foodstuff liquids. The principal applications of microfiltration are low temperature removal of bacteria, and clarification of agro-foodstuff liquids.

The present invention exploits the general technique of microfiltration for the extraction of lysozyme from white of egg and/or whole of egg. The results obtained with the process are particularly valuable and surprising. Firstly, the extraction is perfectly selective, because the microfiltrate passing through the membrane contains at least a part of the lysozyme of the starting material based on white of egg or whole of egg, but to the exclusion of the other proteins of the starting material. The product retained by the membrane is a white of egg or whole of egg or retentate (egg product enriched in proteins and possibly in lipids) devoid of a part of its lysozyme but retaining all the properties of the natural product (pH, swelling properties, and the relative composition in respect of proteins other than the lysozyme).

According to the process of the invention, the yield of extraction of lysozyme from white of egg or whole of egg is from 50 to 80% or even more.

Contrary to the known precipitation technique, the invention makes it possible to handle the treated white of egg or whole of egg for only a very short period, of less than 6 hours. Finally, the process is perfectly suitable for industrial implementation because of the extreme simplicity of the working conditions and the low cost of extraction which it entails.

The conditions under which the microfiltration is carried out are not critical. The working parameters, such as the temperature, the pressure and the rate of flow of the product depend solely on the type of membrane used. The membranes are of a type usual in microfiltration and are capable of separating particles having a size of, approximately, between 0.02 micron and 10 microns. As is conventionally the case, the membranes are assembled in the form of devices referred to as modules. It is generally advantageous to work at temperatures above ambient temperature so as to facilitate bringing the fluid product into contact with the membrane. As is shown by the examples which follow, temperatures of the order of 40° to 45° C. have proved suitable. The process involves passing the fluid starting material over the membrane under a positive pressure. It is however, advantageous to employ known hydrodynamic means to limit the increase in thickness and the density of texture of the polarisation layer, for example by causing the liquid based on white of egg to flow at a speed equal to or greater than 5 m/s and limiting the entry pressure to the extent that the design of the module allows this. As is illustrated in the examples which follow, pressures of less than 5 bars and especially of the order of 2 to 3 bars have proved suitable.

To carry out the process of the invention, white of egg can be used directly, but it is preferred to dilute it beforehand with water containing a soluble salt such as sodium chloride or a soluble sugar such as glucose or sucrose, so as to obtain both a fluid starting material suitable for microfiltration and a higher lysozyme extraction yield. It is also possible to use whole of egg directly, but it is preferred to dilute it first with water containing a soluble salt, such as sodium chloride, or a soluble sugar, such as glucose or sucrose.

According to the present invention, an antioxidant substance allowed under present legislation, such as ascorbic acid, can be added beforehand to the whole of egg so as to avoid any damage to the lipids of the product during the microfiltration treatment.

As has been mentioned above, all the mixtures thus employed fall within the scope of the present invention and constitute the starting material, based on white of egg, to which the process relates.

It will also be noted that, as is usual in the technique of microfiltration, it is advantageous in certain cases—though it is not absolutely necessary—to use diafiltration of the white of egg or whole of egg, whether natural or diluted, by adding to the starting material an amount of water equal to the amount of microfiltrate which issues. Examples 1, 2, 4 and 5 below illustrate this technique.

The invention also relates to the products obtained by the process described above. The white of egg or whole of egg, or the respective retentates, from which the lysozyme has been removed can be used as they are, in a liquid or frozen form, or in a form concentrated by evaporation, optionally supplemented with additives (salts, sugars or ascorbic acid), or in a dried form. The lysozyme contained in the microfiltrate can, in accordance with a known process, be concentrated and purified by ultrafiltration on a membrane of porosity between 2,000 and 10,000 Daltons and then be dehydrated by freeze-drying or be spray-dried. The invention relates to a product based on white of egg and/or whole of egg, depleted in lysozyme, but in other respects retaining all the other properties and characteristics of the natural product, as well as to the lysozyme of high purity which has been extracted by the process of the invention.

The invention will now be illustrated, without in any way being limited, by the examples which follow:

EXAMPLE 1

The chalazae are first removed from 7 kg of white of egg, containing 4.5 g of lysozyme/kg, which are homogenised. They are then diluted with 14 kg of saline water containing 5 g of sodium chloride/kg. The mixture is microfiltered by means of a microfiltration device comprising a SFEC microfiltration module equipped with M 6-4 membranes of surface area equal to 0.113 m². The working conditions are as follows: microfiltration temperature: 40° C., pressure at entry into the microfiltration module: 2 bars, flow rate in the microfiltration module: 1 to 8 m/s, preferably 4 to 6 m/s.

From the start of the microfiltration, a diafiltration of the diluted white of egg is carried out (i.e. an amount of water equal to the amount of microfiltrate which issues is added continuously). The diafiltration lasts for 4 hours and the mixture is then concentrated so as to obtain the initial 7 kg of white of egg. On the other hand, 45 kg of microfiltrate, containing 0.46 g of lysozyme/kg, are collected. The lysozyme extraction yield is 65.7%. This solution is subsequently ultrafiltered in a known manner so as to concentrate the lysozyme. The concentrate obtained is dried or freeze-dried.

EXAMPLE 2

The chalazae are removed from 5.28 kg of white of egg containing 4.08 g of lysozyme/kg, which are homogenised. They are then diluted with 15.84 kg of saline water containing 5 g of sodium chloride/kg. The mixture is microfiltered on a microfiltration device comprising an SFEC M6-1,000 microfiltration module having a membrane surface area of 0.113 m², at a temperature of 42° C., an entry pressure of 2 bars and a flow rate of 6 m/s in the microfiltration module. Diafiltration of the mixture is carried out for 4 hours and the mixture is then concentrated to give the initial 5.28 kg of white of egg. On the other hand, 51.3 kg of microfiltrate containing 0.32 g of lysozyme/kg are collected. The extraction yield is 76%. The microfiltrate is subsequently concentrated by ultrafiltration, in a known manner, and is then dried or freeze-dried.

EXAMPLE 3

To 6.9 kg of chalaza-free and homogenised white of egg are added 13.3 kg of saline water, containing 5 g of salt/kg, and the mixture is heated to 40° C. It is microfiltered on a microfiltration device comprising a Norton module equipped with 0.0248 m² of ceramic membranes having a porosity of 0.5μ. The entry pressure is 2.5 bars and the exit pressure is 0.5 bar. The recirculation speed is 8 m/s. The volume of liquid in the recirculation cell is kept constant by recycling the permeate. The experiment lasts 1 hour 45 minutes. The microfiltration rate varies from 27 liters.h$^{-1}$.m$^{-2}$ to 23 liters.h$^{-1}$.m$^{-2}$. The lysozyme content of the liquid retained by the microfiltration membranes is 2.14 g/kg. The lysozyme content of the microfiltrate is 1 g/kg. The Lysozyme extraction performance under the conditions used thus varies from 23 to 27 g/h/m². The purity of the lysozyme in the microfiltrate at the end of the experiment is about 99%.

EXAMPLE 4

The chalazae are removed from 4 kg of whole of egg containing 3.27 g of lysozyme/kg, which are homogenised. They are then diluted with 16 kg of saline water containing 5 g of sodium chloride/kg. The mixture is microfiltered on an SFEC M6-4 microfiltration module having a membrane surface area of 0.113 m², at a temperature of 44° C., an entry pressure of 2 bars, and a flow rate of 6 m/s in the microfiltration module. Diafiltration of the mixture is carried out for 4 hours and the mixture is then concentrated to give the initial 4 kg of whole of egg. On the other hand, 50.7 kg of microfiltrate containing 0.13 g of lysozyme/kg are collected. The purity of the lysozyme in the microfiltrate is more than 94%. The lysozyme extraction yield is 50%.

EXAMPLE 5

The chalazae are removed from 880 kg of white of egg containing 4.5 g of lysozyme/kg, which are homogenised. They are then diluted with 1,750 kg of saline water containing 5 g of sodium chloride/kg. The mixture is microfiltered on an industrial microfiltration installation comprising an SFEC module of the M6-4 type, having a membrane surface area equal to 5-7 m².

The working conditions are as follows:
Microfiltration temperature: 40° C.
Pressure upon entry into the microfiltration module: 2 to 3 bars.
Flow rate in the microfiltration module: 4 m/s.

From the start of the microfiltration, a diafiltration of the diluted white of egg is carried out. The experiment lasts 5 hours. The mean lysozyme content of the microfiltrate is 0.8 g/kg. The mean lysozyme extraction performance is 24 g/h/m². The mean purity of the lysozyme in the microfiltrate is 80%.

EXAMPLE 6

The chalazae are first removed from 310 kg of white of egg containing 4.21 g of lysozyme/kg, which are homogenised. They are then diluted with 750 kg of saline water containing 5 g of sodium chloride/kg. The mixture is microfiltered on an industrial microfiltration installation comprising an SFEC module of the M6-4 type, having a membrane surface area of 5.7 m².

The working conditions are as follows:
Microfiltration temperature: 42° C.
Pressure upon entry into the microfiltration module: 2 to 3 bars.
Flow rate in the microfiltration module: 5 m/s.

The diluted white of egg is concentrated to give 124 kg of concentrated white of egg having a solids content of 26%. The lysozyme content of the microfiltrate is 0.56 g/kg.

The mean lysozyme extraction yield in the microfiltrate is 40%.

What is claimed is:

1. A process for obtaining lysozyme containing filtrate from a fluid starting material based on white of egg, comprising microfiltering said starting material, under pressure and in tangential flow, through a membrane capable of passing only particles having a size of between about 0.02 micron and 10 microns, to produce said lysozyme-containing microfiltrate.

2. The process as defined by claim 1, wherein said starting material is selected from the group consisting of white of egg, whole of egg, and mixtures thereof.

3. The process as defined by claim 1, wherein, prior to microfiltration, said process comprises diluting said starting material with water containing a soluble salt.

4. The process as defined by claim 1, wherein, prior to microfiltration, said process comprises diluting said starting material with water containing a soluble sugar.

5. The process as defined by claim 2, wherein said pressure is less than 5 bars and said tangential flow is between about 1 and 8 meters/second.

6. The process as defined by claim 5, wherein said pressure is between about 2 and 3 bars.

7. The process as defined by claim 2, wherein said process is carried out for between about 1 and 6 hours.

8. The process as defined by claim 5, wherein said process is carried out for between about 1 and 6 hours.

9. The process as defined by claim 1, wherein said starting material further comprises an antioxidant.

10. The process as defined by claim 1, further comprising diafiltrating said starting material during microfiltration by continuously adding thereto an amount of water equal to the amount of microfiltrate issuing therefrom.

11. The process as defined by claim 1, further comprising first ultrafiltrating and then dehydrating said microfiltrate.

* * * * *

UNITED STATES PATENT AND TRADEMARK OFFICE
CERTIFICATE OF CORRECTION

PATENT NO.  : 4,721,674

DATED       : Jan. 26, 1988

INVENTOR(S) : Alain LEPIENNE et al.

It is certified that error appears in the above-identified patent and that said Letters Patent is hereby corrected as shown below:

At column 1, line 15, change "bactericidial" to ---bactericidal---.

At column 1, line 55, change "proerties" to ---properties---.

At column 1, line 57, delete "can".

At column 1, line 57, insert ---been--- after "have" and before "identified".

At column 2, line 1, change "Тnese" to ---There--- (2nd occurrence).

At column 2, line 15, change "starting" to ---salting---.

At column 2, line 56, insert ---,--- after "yields".

At column 5, line 54, change "Lysozyme" to ---lysozyme---.

Signed and Sealed this

Twenty-first Day of April, 1992

Attest:

HARRY F. MANBECK, JR.

*Attesting Officer*    *Commissioner of Patents and Trademarks*